(12) United States Patent
Wurmfeld et al.

(10) Patent No.: US 8,706,194 B2
(45) Date of Patent: Apr. 22, 2014

(54) POSITION DETECTION IN A MAGNETIC FIELD

(75) Inventors: David Wurmfeld, Melbourne, FL (US); Matthew S. Solar, Indialantic, FL (US)

(73) Assignee: Medtronic, Inc., Minneapolis, MN (US)

( * ) Notice: Subject to any disclaimer, the term of this patent is extended or adjusted under 35 U.S.C. 154(b) by 1269 days.

(21) Appl. No.: 12/551,131

(22) Filed: Aug. 31, 2009

(65) Prior Publication Data

US 2009/0318799 A1    Dec. 24, 2009

Related U.S. Application Data

(62) Division of application No. 11/324,133, filed on Dec. 30, 2005, now Pat. No. 7,603,161.

(51) Int. Cl.
*A61B 5/05* (2006.01)

(52) U.S. Cl.
USPC ........... 600/424; 600/407; 600/410; 600/428; 600/431; 606/130

(58) Field of Classification Search
USPC ............ 600/424, 410, 431; 606/130; 250/221
See application file for complete search history.

(56) References Cited

U.S. PATENT DOCUMENTS

| | | | | |
|---|---|---|---|---|
| 4,151,834 A | * | 5/1979 | Sato et al. | 600/446 |
| 4,170,226 A | * | 10/1979 | Albainy et al. | 600/480 |
| 5,129,725 A | * | 7/1992 | Ishizuka et al. | 356/617 |
| 5,150,715 A | * | 9/1992 | Ishiguro et al. | 600/463 |
| 5,211,176 A | * | 5/1993 | Ishiguro et al. | 600/463 |
| 5,442,858 A | | 8/1995 | Wolters et al. | |
| 5,690,110 A | * | 11/1997 | Tanaka | 600/446 |
| 5,794,621 A | | 8/1998 | Hogan et al. | |
| 5,877,732 A | | 3/1999 | Ziarati | |
| 5,917,182 A | * | 6/1999 | Ishizuka | 250/237 G |

(Continued)

FOREIGN PATENT DOCUMENTS

| | | |
|---|---|---|
| DE | 29821831 | 3/1999 |
| EP | 1477115 A1 | 11/2004 |

(Continued)

OTHER PUBLICATIONS

International Search Report and Written Opinion mailed Jun. 26, 2007 for PCT/US2006/049572 claiming benefit of U. S. Appl. No. 11/324,133, filed Dec. 30, 2005.

(Continued)

*Primary Examiner* — Baisakhi Roy
(74) *Attorney, Agent, or Firm* — Harness, Dickey & Pierce, PLC

(57) ABSTRACT

This patent document discusses assemblies and methods for remotely detecting a position of a surgical instrument in the presence of a magnetic field. In varying examples, a position detection system includes an encoder coupled to move in concert with the instrument. The encoder includes an a translucent substrate and light blocking indicia disposed thereon. A light source and a light detector array are effectively disposed outside of the magnetic field. Light from the light source is carried to an encoder first side using an input optical fiber, while the light passing through the encoder is received at an encoder second side by an output optical fiber. The light received by the output optical fiber is transmitted to the light detector array, which converts the received light to position representative electrical signals. Such signals are subsequently transmitted to a control module adapted to formulate and convey a position of the instrument.

13 Claims, 10 Drawing Sheets

(56) References Cited

U.S. PATENT DOCUMENTS

| | | | |
|---|---|---|---|
| 5,992,970 A * | 11/1999 | Unosawa et al. | 347/37 |
| 6,418,337 B1 | 7/2002 | Torchia et al. | |
| 7,135,673 B2 | 11/2006 | Saint Clair | |
| 7,603,161 B2 * | 10/2009 | Wurmfeld et al. | 600/424 |
| 2001/0022611 A1 * | 9/2001 | Sousa | 347/234 |
| 2002/0003206 A1 * | 1/2002 | Culver | 250/221 |
| 2002/0067263 A1 * | 6/2002 | Tafoya et al. | 340/572.1 |
| 2002/0087065 A1 * | 7/2002 | Yanof et al. | 600/410 |
| 2002/0156372 A1 * | 10/2002 | Skakoon et al. | 600/431 |
| 2003/0097060 A1 * | 5/2003 | Yanof et al. | 600/424 |
| 2003/0098844 A1 | 5/2003 | Melnyk | |
| 2003/0209658 A1 * | 11/2003 | Iguchi et al. | 250/231.13 |
| 2004/0181148 A1 * | 9/2004 | Uchiyama et al. | 600/425 |
| 2004/0242993 A1 | 12/2004 | Tajima | |
| 2006/0122628 A1 | 6/2006 | Solar et al. | |
| 2007/0058172 A1 * | 3/2007 | Van Der Pasch et al. | 356/494 |
| 2007/0203404 A1 * | 8/2007 | Zysk et al. | 600/310 |
| 2009/0118743 A1 * | 5/2009 | Solar et al. | 606/130 |
| 2013/0131650 A1 * | 5/2013 | Whitman et al. | 606/1 |

FOREIGN PATENT DOCUMENTS

| | | |
|---|---|---|
| GB | 2188144 A | 9/1987 |
| JP | 58019507 A | 2/1983 |
| WO | WO-0133165 A1 | 5/2001 |

OTHER PUBLICATIONS

International Preliminary Report on Patentability mailed Apr. 17, 2008 for PCT/US2006/049572 claiming benefit of U. S. Appl. No. 11/324,133, filed Dec. 30, 2005.

* cited by examiner

POSITION DETECTION IN A MAGNETIC FIELD

CROSS-REFERENCE TO RELATED APPLICATIONS

This application is a divisional of U.S. Ser. No. 11/324,133, filed Dec. 30, 2005. The disclosure of the above application is incorporated herein by reference.

FIELD

This patent document pertains generally to monitoring the position of a surgical instrument. More particularly, but not by way of limitation, this patent document pertains to remote position detection of a surgical instrument in the presence of a magnetic field.

BACKGROUND

In the treatment of some diseases or defects associated with a patient, it has been found necessary to access specific targets within the patient. For example, in neurosurgery, it has been found necessary to access specific targets within the patient's brain. In neurosurgery, the specific targets are typically located and identified by one of a number of techniques. Sometimes the target can be visualized using magnetic resonance imaging (MRI). MRI has been developed as an imaging technique adapted to obtain both images of anatomical features of patients as well as some aspects of the functional activities of biological tissue.

Once a target has been identified, neurosurgery involves making a drill hole in the relatively thick bony structure surrounding the brain (i.e., the skull). The drill hole is made by a surgeon at a desired entry point using a surgical drill. The surgeon then typically guides (e.g., using trajectory guide tubes) one or more surgical instruments or observation tools (e.g., electrodes—recording or stimulating, cannulas, needles, biopsy instruments, catheters or other types of probes or devices) through the entry hole to the specific targets within the brain. At least two challenges involved in neurosurgery include staying oriented within the brain, and directing instruments to a desired depth therein. To satisfy the former of these two challenges, according to one technique, both the aiming of the instrument guide and the subsequent introduction of the instrument are conducted while a patient's skull is positioned within an enclosure (i.e., a bore) of an MRI scanner. Through the use of the MRI scanner, the surgeon is able to verify the orientation of each instrument introduced. Unfortunately, however, using such technique the surgeon is currently unable to also remotely determine the position (e.g., depth) of the instrument introduced. Instead, to determine the depth of the instrument, the surgeon must leave his/her position near an imaging display and enter the MRI-generated magnetic field and manually read the instrument depth.

Some drawbacks of the MRI technique are rooted in the fact that the corresponding magnetic field often presents problems with electrical components, such as the electrical components of conventional electronic measuring apparatus. The use of electrical components may not work in the strong magnetic field surrounding an MRI scanner for at least three reasons. First, their components (e.g., metal wires, electrical components, etc.) may experience a force in the magnetic field, creating a safety hazard for the patient. Second, the accuracy with which such components operate may be affected by the magnetic field. Third, it puts patients at risk for burns due to eddy currents generated within conductive components.

It is with this recognition of the foregoing state of the technology that the present assemblies and methods providing remote position detection in an electromagnetic field have been conceived and are now set forth in text and drawings associated with this patent document.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in this patent document.

DETAILED DESCRIPTION

Figure 1:
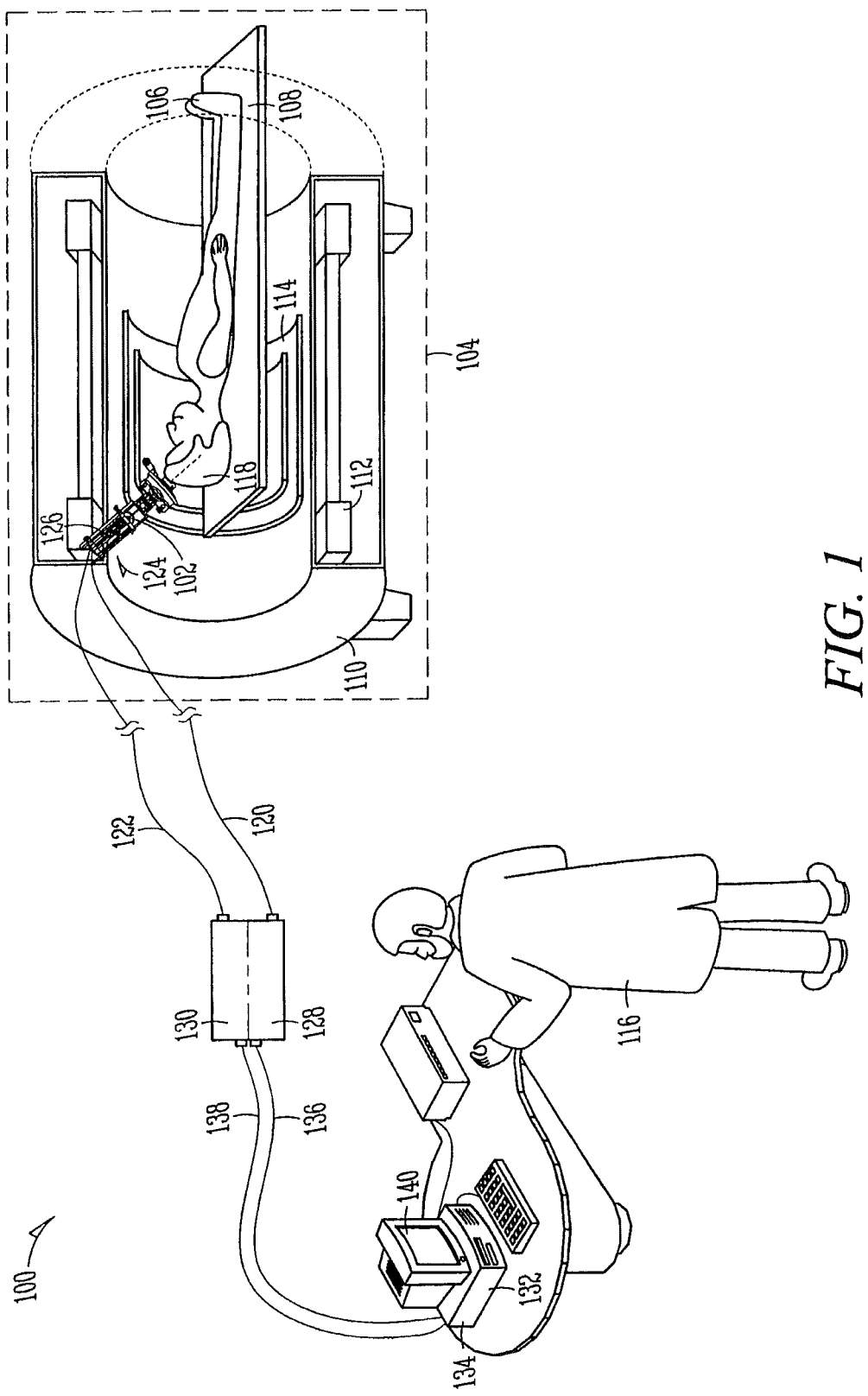
FIG. 1 is a schematic view illustrating an assembly for providing remote position detection in a magnetic field, as constructed in accordance with at least one embodiment.

The following detailed description includes references to the accompanying drawings, which form a part of the detailed description. The drawings show, by way of illustration, specific embodiments in which the present assemblies and methods may be practiced. These embodiments, which are also referred to herein as "examples," are described in enough detail to enable those skilled in the art to practice the present assemblies and methods. The embodiments may be combined or varied, other embodiments may be utilized or structural, logical, or electrical changes may be made without departing from the scope of the present assemblies and methods. It is also to be understood that the various embodiments of the present assemblies and methods, although different, are not necessarily mutually exclusive. For example, a particular feature, structure or characteristic described in one embodiment may be included within other embodiments. The following detailed description is, therefore, not to be taken in a limiting sense, and the scope of the present assemblies and methods are defined by the appended claims and their legal equivalents.

In this document, the terms "a" or "an" are used to include one or more than one; the term "or" is used to refer to a nonexclusive or unless otherwise indicated; the term "instrument" is used to refer to any surgical instrument or observation tool; and the term "subject" is used to include the term "patient." In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

Introduction and Examples

In addition to the aiming and guiding of instruments into a subject, the position (e.g., depth) of such instruments being introduced is also important. For example, a neurosurgeon may first introduce a brain-activity recording electrode to a particular depth within the brain that exhibits a desired degree of brain-activity. The neurosurgeon may then want to remove the recording electrode and introduce a drug or cell delivery catheter or stimulation electrode to that same depth. As discussed above, through the use of a MRI scanner, the surgeon is able to verify the orientation of the instruments being introduced. Unfortunately, however, the surgeon is currently unable to also remotely determine the depth of the instruments being introduced due to problems the (MRI-generated) magnetic field creates with components of conventional electronic measuring techniques.

Advantageously, the present assemblies and methods provide the capability of optically encoding an instrument's depth (i.e., converting the mechanical position of the instrument into representative electrical signals by means of, among other things, a patterned scale, a light source and photosensitive elements) in the presence of the (typically) strong magnetic field associated with a MRI scanner or similar, such that the depth information can be conveyed to a neurosurgeon located remotely, i.e., outside of the magnetic field. The present assemblies and methods, by carrying optical signals (via one or more optical fibers) in lieu of (conductive) electrical components, avoid the drawbacks associated with MRI-generated magnetic fields. (Notably, optical fibers transmit light rather than electrons and therefore, neither radiates magnetic fields nor is susceptible to magnetic fields surrounding it). Several other advantages are also made possible by the present assemblies and methods including adequate patient isolation (e.g., from eddy currents) with good instrument performance. In addition, the present assemblies and methods are easy and economical to manufacture, maintain, and use. Furthermore, the present assemblies and methods allow for sub-micrometer position resolution (e.g., position $+/-0.5\times10^{-6}$ meters).

FIG. 1 is a schematic view illustrating an assembly 100 for providing remote position (e.g., depth) detection of one or more instruments 102 in a magnetic field 104. As shown, a subject 106 disposed on a support table 108 is placed in magnetic field 104, which is generated by, for example, a MRI scanner 110. MRI scanner 110 includes one or more magnets 112, which are shown sectioned in half to reveal subject 106 therewithin. Subject 106 is further surrounded by a set of (cylindrical) magnetic field gradient coils 114 (also shown sectioned in half) adapted to create magnetic field gradients of a predetermined strength at predetermined times. Gradient coils 114 generate magnetic field gradients in three mutually orthogonal directions.

Once the desired portion of subject 106 to be scanned is in or near the center or isocenter of magnetic field 104, the MRI scan may begin. In this example, the head region of subject 106 (into which instrument 102 is shown inserted) is located in the approximate center of the one or more magnets 112 and gradient coils 114. With such positioning and in conjunction with radio wave pulses of energy, MRI scanner 110 picks out points inside the subject's brain 118 and asks it, essentially, "what type of tissue are you?" In this way, MRI scanner 110 goes through brain 118 point-by-point, building up a 2-D or 3-D map of tissue types (see FIGS. 2A, 2B). Non-tissue points are also picked up by MRI scanner 110. As a result of this process, MRI scanner 110 provides a surgeon 116 with information regarding an orientation of each instrument 102 introduced into subject 106, in addition to diseases or defects of brain 118 (see FIGS. 2A, 2B). Unfortunately, however, using previous remote position detection assemblies and methods in conjunction with MRI scanner 110, the surgeon 116 was unable to also remotely determine the position of instrument(s) 102 because of the MRI-associated magnetic field 104 and its effect on conductive components required in previous remote position detection assemblies and methods.

By carrying optical signals (via one or more optical fibers 120, 122) in lieu of conductive components, the present assemblies 100 and methods avoid the drawbacks associated with MRI-generated magnetic fields and thereby can provide position (including both absolute and relative position), in addition to orientation, information to surgeon 116. In this example, position detection assembly 100 is shown coupled to a drive and trajectory guide assembly 124 (see, e.g., FIGS. 5, 6) and includes an encoder 126, a light source 128, at least one input optical fiber 120, an input electrical cable 136, a light detector array 130, at least one output optical fiber 122, an output electrical cable 138, and one or both of a first control module 132 or a second control module 134. For simplicity purposes, position detection assembly 100 may be conceptualized as including a light input subsystem, an optical target, and a light output subsystem. The light input subsystem typically includes input electrical cable 136, light source 128, input optical fiber(s) 120, and first control module 132. The optical target typically includes encoder 126 having one or both of relative position indicia or absolute position indicia thereon. The light output subsystem typically includes output optical fiber(s) 122, light detector array 130, output electrical cable 138, and second control module 134.

Referring initially to the light input subsystem, in this example, first control module 132 is disposed far enough away from magnetic field 104 surrounding subject 106 so that it neither influences nor is influenced by such field 104 to any appreciable degree. Input electrical cable 136 is connected at one end to module 132 and at the other end to light source 128. Similar to first control module 132, light source 128 is disposed far enough away from magnetic field 104. Input electrical cable 136 transmits electrical signals from first control module 132 to light source 128, which acts as a transducer to convert the electrical signals from the module into light signals. The at least one input optical fiber 120 carries the light signals from light source 128 to a point adjacent a first side of encoder 126. In one example, the at least one input optical fiber 120 includes a plurality of input optical fiber, which carry the light signals from light source 128 to a position near encoder 126.

Encoder 126, as noted, includes a first side and an oppositely positioned second side. In addition, encoder 126 comprises a translucent substrate and one or more light blocking indicia disposed on the substrate. In one example, the one or more light blocking indicia disposed on the substrate include two rows of alternating opaque and translucent graduation marks. In one such example, the two rows of alternating opaque and transparent graduation marks are placed parallel to one another or are placed laterally offset from one another by a fraction of the width of the graduation marks. In another example, the fraction of the width of the graduation marks includes a range from one-eighth to one-fourth of the width of the graduation marks, which causes (in one example) a phase shift of approximately thirty-eight degrees between electrical signals generated by light detector array 130.

In a further example, the one or more light blocking indicia include at least one absolute position marker. The at least one absolute position marker may include one or more scanning field tracks and a series of alternative opaque and translucent marks located in the one or more scanning field tracks. The series of opaque and translucent marks may represent a binary number that encodes an absolute position on the translucent scale. The binary number encoding, in one example, uses Excess Gray code. In this way, among others, encoder 126 provides an optical target located within magnetic field 104, which light from light source 128 via input optical fiber(s) 120 attempts to pass through.

Referring next to the light output system, which comprises at least one output optical fiber 122 for receiving optical (i.e., light) signals extending through encoder 126 and transmitting such light signals outside of magnetic field 104 to light detector array 130. Light detector array 130, acting as one or more photodetectors or photodiodes, converts the light signals received by the at least one output optical fiber 122 to electrical signals impressed on output electrical cable 138. In one example, light detector array 130 generates electrical signals representative of each of one or more rows of (alternating opaque and translucent) graduation marks when the rows are scanned by illuminating them with one or more input optical fibers 120 and detecting the light passing through the marks with one or more output optical fibers 122. The representative electrical signals may provide, among other things, information relating to instrument's 102 absolute or relative position (including distance or direction information) or speed upon, for example, as little as 0.1 mm of travel.

Advantageously, the absolute position ability of the present assemblies and methods avoids loss of position data upon power-down. This is because the present assemblies can be reinitialized on power-up by searching for an index (i.e., one or more absolute indicia marks) and resetting the position counter accordingly. Thus, even following a power loss, by way of a very short travel, such as 0.2 mm, (in either direction starting from anywhere), a user knows where instrument 102 is positioned with little to no error.

Output electrical cable 138 is connected at one end to light detector array 130 and at the other end of a second control module 134. Second control module 134 is disposed remotely outside magnetic field 104. As shown, first and second control modules 132, 134, respectively, may be integral and include a display 140. Display 140 may be configured to enable surgeon 116 to quickly recognize the position (e.g., depth) or orientation information of the one or more instruments 102. It is to be appreciated that magnetic fields 104, such as the radiofrequency (referred to as "RF") fields created by MRI scanner 110, have no sharp termination or boundary lines. Accordingly, when an element is "located outside a magnetic field," it is disposed where the magnetic field does not interfere with operation of the element or operation of the element does not interfere with the function of the magnetic field.

Figure 2A:
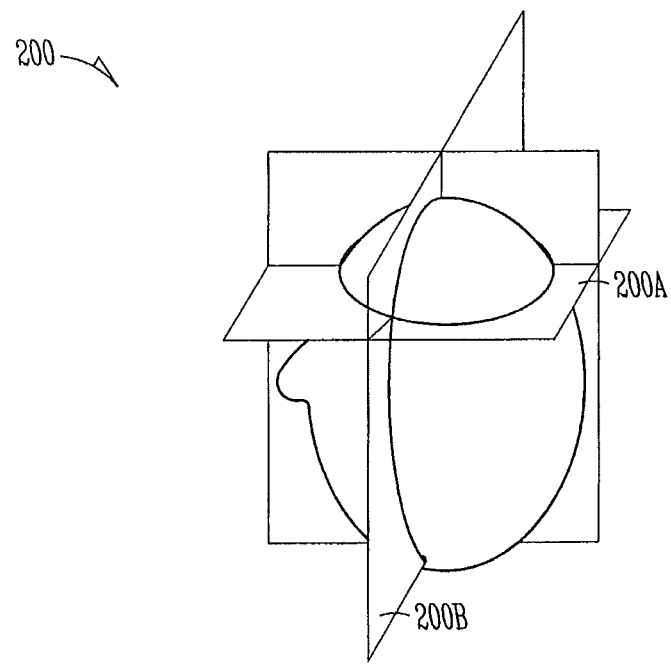
FIG. 2A is a schematic view illustrating exemplary imaging planes made possible through the use of MRI techniques.
Figure 2B:
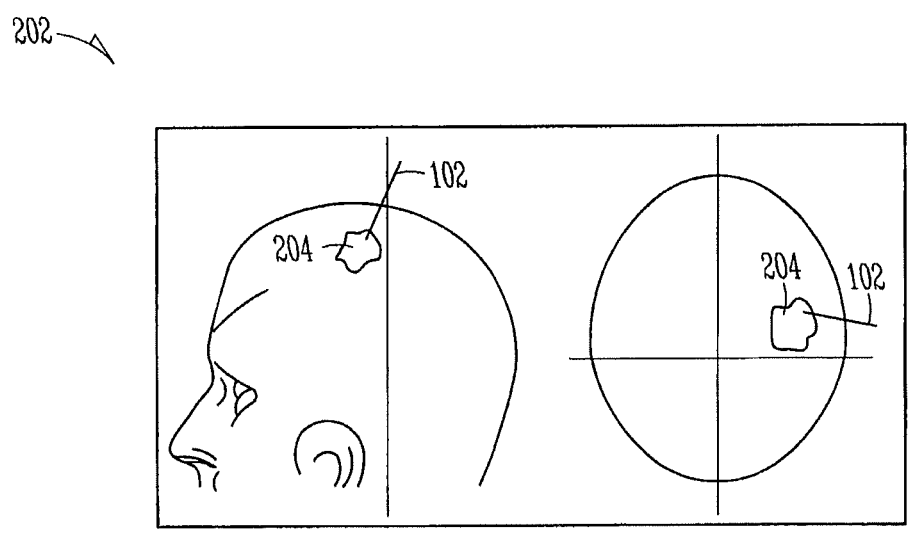
FIG. 2B illustrates exemplary MRI-produced planar images of a subject's brain including one or more diseases or defects.

FIGS. 2A, 2B relate to imagery made possible by MRI scanning techniques. Specifically, FIG. 2A illustrates exemplary imaging planes 200 made possible by the use of MRI techniques, while FIG. 2B illustrates exemplary MRI-produced planar images 202. Unlike other imaging techniques, MRI has the ability to image in any plane, such as, planes 200A, 200B. The imaging capabilities of MRI systems allows a surgeon 116 (FIG. 1) to gain an unparalleled view inside a subject's body 106 (FIG. 1). By changing exam parameters, the MRI system can cause tissues in, or foreign instruments 102 introduced into, the body to take on different appearances than their surroundings. This is very helpful to surgeon 116 in determining the orientation or depth of foreign instrument(s) 102 or for detecting one or more diseases or defects 204 of the brain 118 (FIG. 1).

Figure 3:
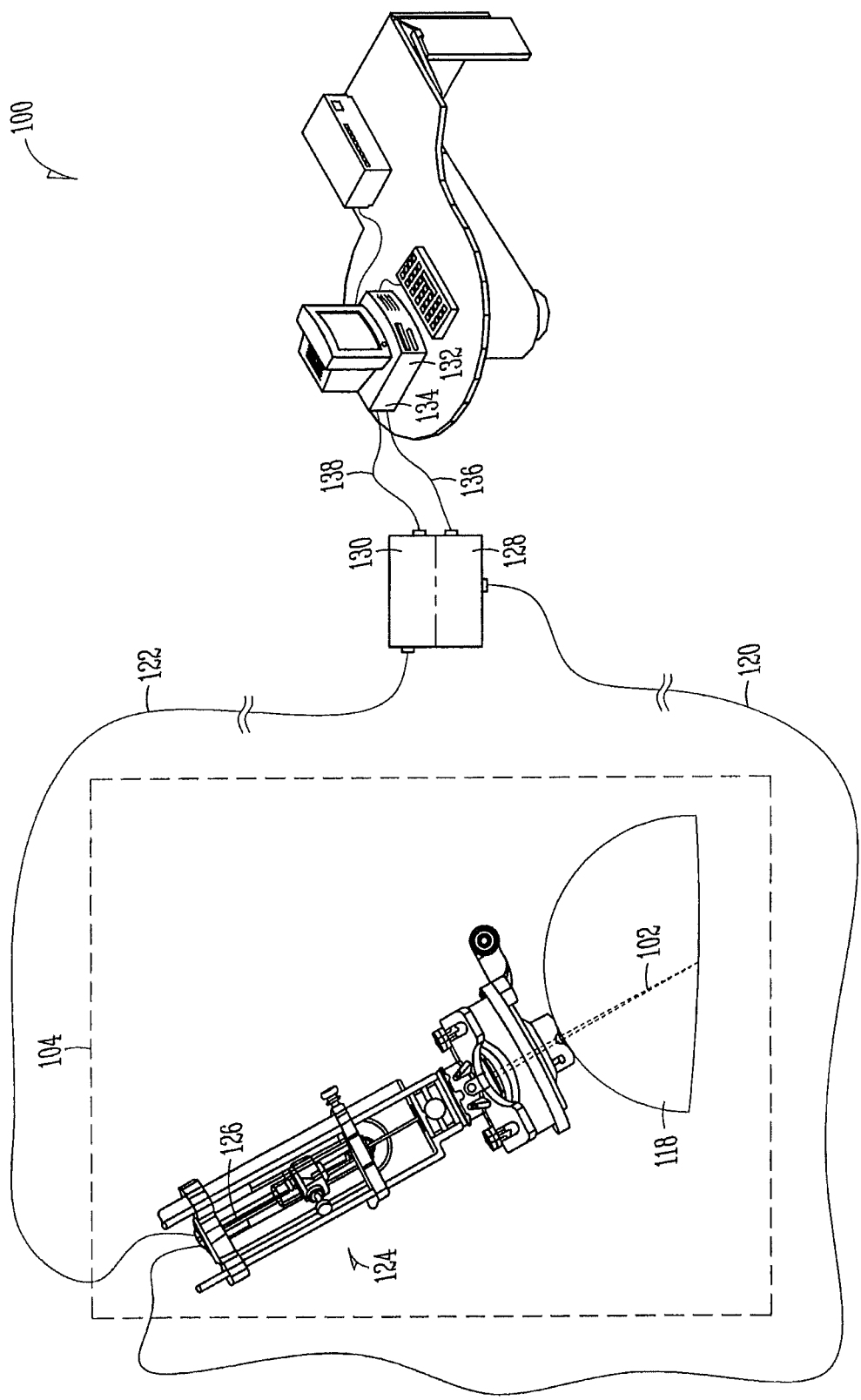
FIG. 3 is a schematic view illustrating an assembly for providing remote position detection in a magnetic field, as constructed in accordance with at least one embodiment.

FIG. 3 illustrates an enlarged view (relative to FIG. 1) of an assembly 100 for providing remote position (e.g., depth) detection of one or more instruments 102 in the presence of a magnetic field 104. As shown, position detection assembly 100 is coupled to a drive and trajectory guide assembly 124 used for, among other things, the introduction and removal of the one or more instruments 102. One example of drive and trajectory guide assembly 100 is described in more detail in associated with FIG. 5 (discussed below) and in commonly assigned Solar et al., U.S. patent application Ser. No. 11/005,607, entitled "INSTRUMENT GUIDING STAGE APPARATUS AND METHOD FOR USING THE SAME," which was filed on Dec. 4, 2004, the disclosure of which is incorporated herein by reference in its entirety. As discussed above, position detection assembly 100 generally includes a light input subsystem, an optical target, and a light output subsystem.

Light input subsystem comprises a first control module 132, an input electrical cable 136, a light source 128, and one or more input optical fibers 120. Light output subsystem comprises one or more output optical fibers 122, a light detector array 130, an output electrical cable 138, and a second control module 134. Optical target comprises an encoder 126 having one or both of relative position indicia or absolute position indicia disposed thereon.

To obtain the desired magnetic field compatibility (e.g., with MRI scanner 110 (FIG. 1)), the present assemblies 100 and methods use one or more input optical fibers 120 to transmit light from light source 128 to within magnetic field 104, such as a point adjacent a first side of encoder 126. Ends of these optical fibers 120 are attached to drive and trajectory guide assembly 124 (e.g., via a housing 700, see FIG. 7) and arranged so that the transmitted light is directed toward, and portions of the light through, encoder 126. Similarly, ends of one or more output optical fibers 122 are attached to drive and trajectory guide assembly 124 (e.g., via a housing 700) and arranged to receive light passing through encoder 126. Encoder 126, by being comprised of a translucent substrate including, for example, glass or plastic with one or more light blocking indicia disposed thereon, allows some rays of light therethrough while blocking others.

To this end, the present position detection assembly 100 includes an encoder movably mounted relative to one or both of the input optical fibers 120 or the output optical fibers 122 and stationarily mounted relative to the one or more surgical instruments 102 introduced into a subject's brain 118. For instance, encoder 126 may be mounted to a second stage 504 (FIG. 5) of drive and trajectory guide assembly 124, while ends of optical fibers 120, 122 are coupled to a first stage 506 (FIG. 5) of assembly 124. In this way, movement of the one or more instruments 102 results in movement of encoder 126, which further results in movement of the one or more light blocking indicia disposed on encoder 126. The movement of the light blocking indicia creates a pattern by blocking some light rays from passing through encoder 126 while allowing other light rays to pass through. This pattern of block and unblocked light rays is received by output optical fiber(s) 122 and transmitted out of magnetic field 104 to light detector array 130. Light detector array 130, which may comprise one or more photodetectors or photodiodes, is configured to convert the light signals to representative electrical signals which are then sent to second control module 134 for formulation and conveyance (to surgeon 116 (FIG. 1)) of an instrument 102 position.

Figure 4:
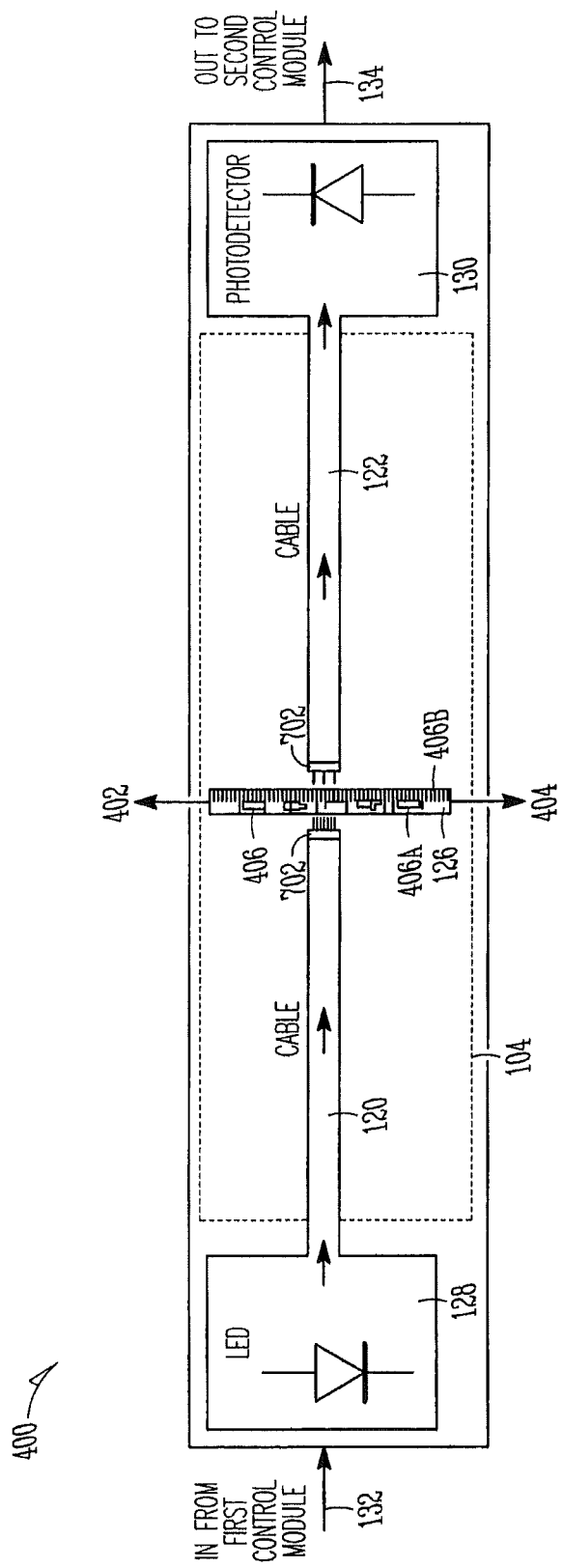
FIG. 4 is a block diagram illustrating portions of an assembly for providing remote position detection in a magnetic field, as constructed in accordance with at least one embodiment.

FIG. 4 is a block diagram 400 illustrating portions of an assembly 100 for providing remote position (e.g., depth) detection of one or more instruments 102 (FIG. 1) in a magnetic field 104. In this example, a first control module 132 (FIG. 1) produces and sends (via an input electrical cable 136 (FIG. 1)) one or more electrical signals to a light source 128, which converts the one or more electrical signals into one or more light signals. The light signals are transmitted, via at least one input optical cable 120, through a lens 702, to an encoder 126 movable (in concert with the one or more instruments 102) in one or more directions 402, 404. As shown, encoder 126 includes one or more light blocking indicia 406, such as absolute position indicia 406A or relative position indicia 406B. Through movement of encoder 126, the light blocking indicia 406 create a unique pattern of emitted light through encoder 126. This unique pattern of emitted light is received by at least one output optical cable 122, after being focused by lens 702, and transmitted to a light detector array 130. Light detector array 130 decodes the unique pattern of emitted light signals and sends electrical signals indicative of an instrument position to a second control module 134 (via an output electrical cable 138). In varying examples, position detection assembly 100 may include one or more optical regenerators to boost the light signals as they travel through optical fibers 120 or 122.

As discussed above, the position detection assembly 100 disclosed herein may, in one example, be used in conjunction with a drive and trajectory guide assembly 124, such as that disclosed in commonly assigned Solar et al., U.S. patent application Ser. No. 11/005,607, entitled "INSTRUMENT GUIDING STAGE APPARATUS AND METHOD FOR USING THE SAME," which was filed on Dec. 4, 2004. To this end, FIGS. 5, 6 illustrate how position detection assembly 100 may be used with a drive and trajectory guide assembly 124.

Figure 5:
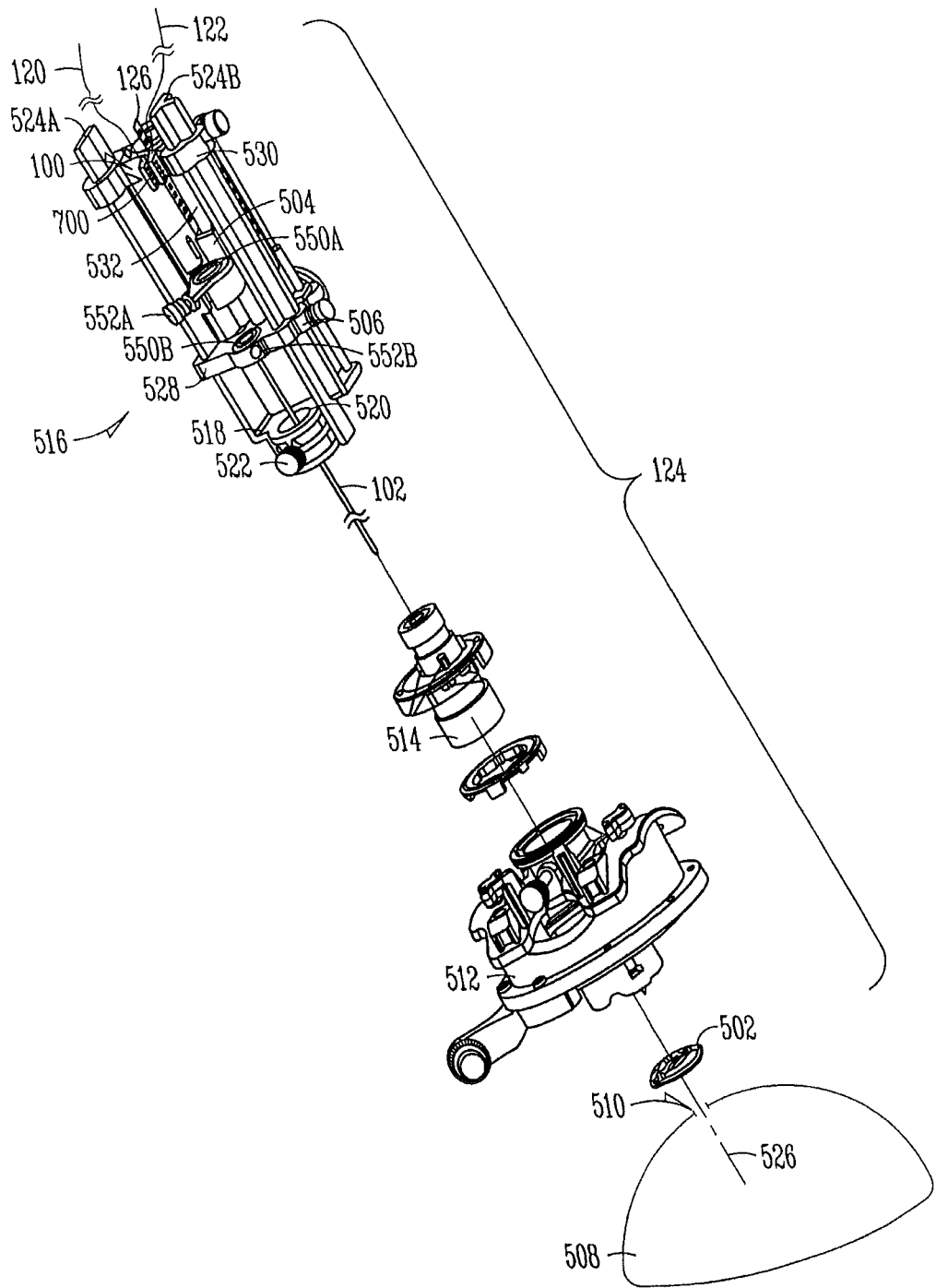
FIG. 5 is an isometric view illustrating portions of an assembly for providing remote position detection in a magnetic field coupled to an instrument drive and trajectory guide assembly, as constructed in accordance with at least one embodiment.
Figure 6:
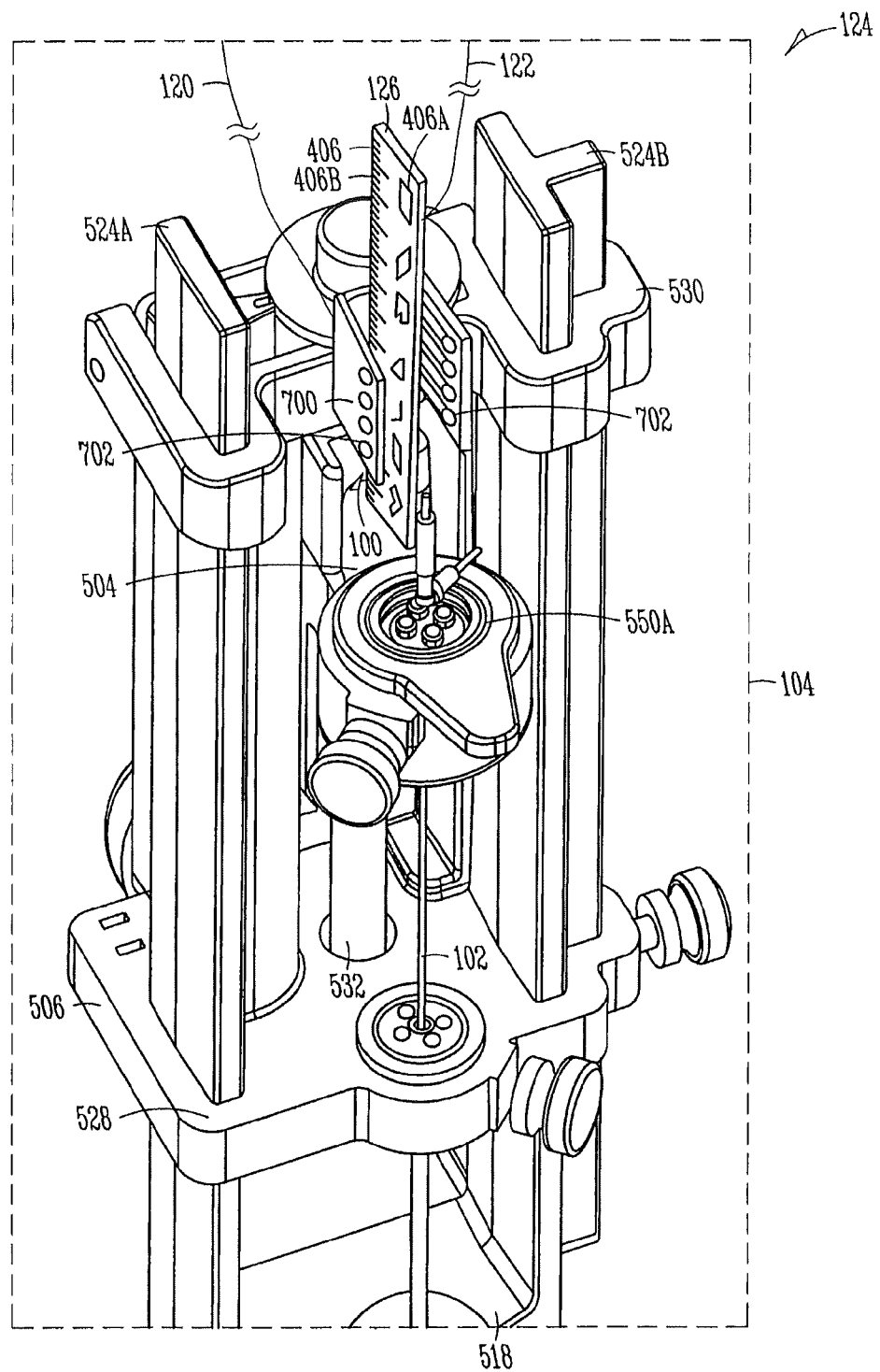
FIG. 6 is an isometric view illustrating portions of an assembly for providing remote position detection in a magnetic field coupled to an instrument drive and trajectory guide assembly, as constructed in accordance with at least one embodiment.

Referring first to FIG. 5, which provides an isometric view illustrating portions of position detection assembly 100 coupled to portions of drive and trajectory guide assembly 124. As shown, an instrument immobilizer 502, configured to attach to a skull 508 (surrounding brain 118 (FIG. 1)) around a drill hole 510, in combination with a trajectory guide 512 couples drive and trajectory guide assembly 124 to a subject 106 (FIG. 1). Specifically, instrument immobilizer 502 is screwed to skull 508, while trajectory guide 512 is also screwed to the skull outside of immobilizer 502 with separate screws. Trajectory guide 512 is further coupled to an instrument guide 514 on a top side. A top side of instrument guide 514 is configured to allow a drive assembly 516 to be coupled thereto.

In this example, drive assembly 516 includes a base 518 having a base lumen 520 configured to receive instrument guide 514. A thumb screw 522 or other fixation device extends through base 518 and into base lumen 520 (an axis of which defines an instrument trajectory 526) to engage instrument guide 514 and fixedly couple drive assembly 516 to the same. As shown, base 518 includes two guide rails 524A, 524B to which a first stage 506 is coupled. In this example, first stage 506 includes a lower portion 528 and an upper portion 530. First stage 506 also includes a first stage lumen which houses retaining assembly 550B. An actuator 552B is coupled to and extends through a portion of first stage 506 to retain one or more instruments 102 (e.g., guide tubes) extending through the first stage lumen.

A second stage 504 is movable coupled to first stage 506. In this example, second stage 504 is slidably coupled to first stage 506 by a lead screw 532 or the like. Lead screw 532 extends between lower portion 528 and upper portion 530 and includes threads configured to mate with second stage 504. Additionally, second stage 504 includes a second stage lumen which houses an instrument retaining assembly 550A. An actuator 552A is coupled to and extends through a portion of second stage 504 to retain one or more instruments (e.g., recording electrodes or catheters) extending through the second stage lumen.

Figure 7:
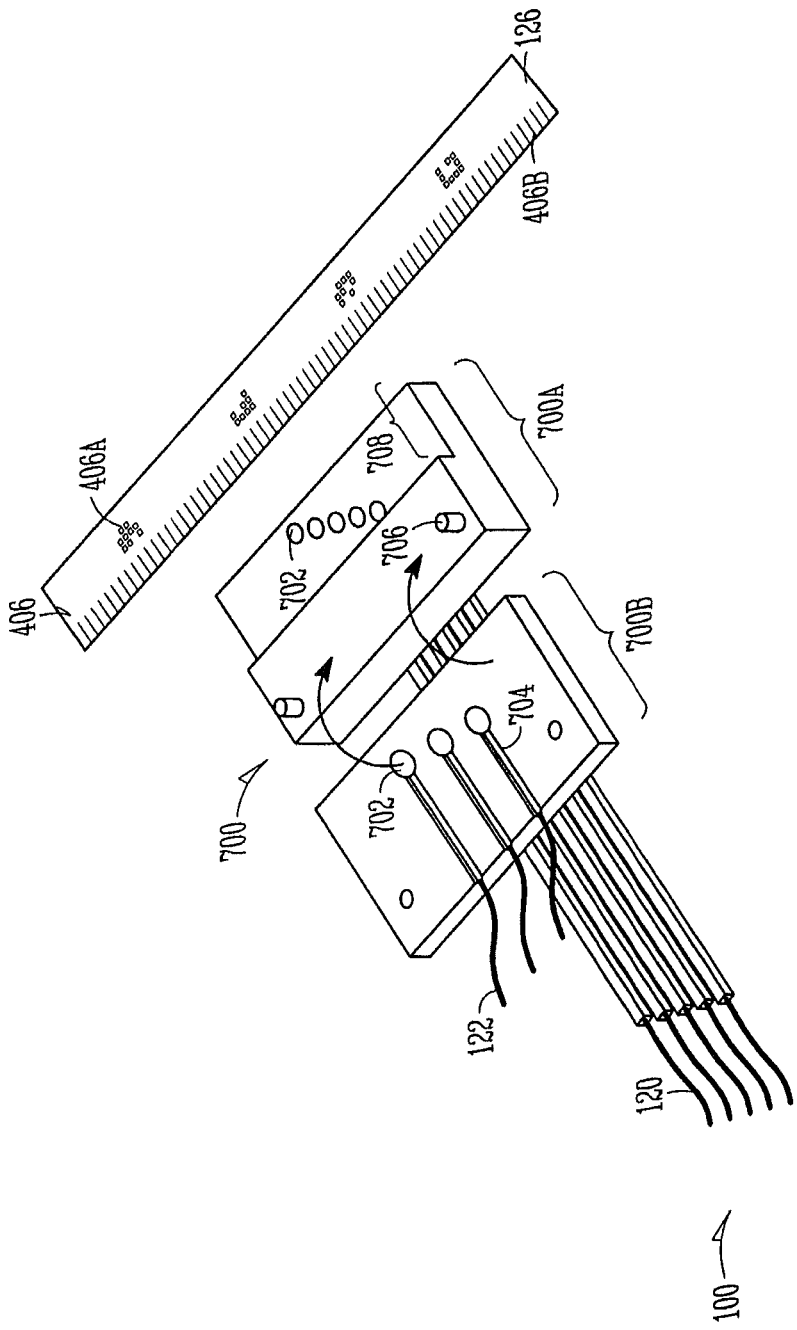
FIG. 7 is an isometric view illustrating portions of an assembly for providing remote position detection in a magnetic field, as constructed in accordance with at least one embodiment.

As shown, but as may vary, ends of at least one input optical fiber 120 and at least one output optical fiber 122 are coupled to first stage 506 near upper portion 530. An encoder 126, on the other hand, is coupled to second stage 504. As a result, encoder 126 is movably mounted relative to both the at least one input optical fiber 120 and the at least one output optical fiber 122. In this example, optical fibers 120, 122 are detachably coupled to first stage 506 by way of one or more position assembly housings 700, one example of which is illustrated in FIG. 7. Advantageously, the position detection assembly 100/drive and trajectory guide assembly 124 combination allows a surgeon 116 (FIG. 1) to, among other things, introduce a brain-activity recording electrode (or similar) to a particular depth within brain 118 and then remove such electrode and introduce a drug or cell delivery catheter or stimulation electrode to that same depth, which can be monitored or verified remotely in the presence of a magnetic field 104 (FIG. 1).

FIG. 6 illustrates an enlarged isometric view (relative to FIG. 5) of an assembly 100 for providing remote position (e.g., depth) detection of one or more instruments 102 in the presence of a magnetic field 104. As shown, assembly 100 is coupled to portions of a drive and trajectory guide assembly 124. In this example, assembly 124 includes a base 518 from which two guide rails 524A, 524B extend. A first stage 506, slidably coupled to guide rails 524A, 524B, includes a lower portion 528 and an upper portion 530. A second stage 504 is movably coupled to first stage 506, such as by way of a lead screw 532 or the like. Lead screw 532 extends between lower portion 528 and upper portion 530 and includes threads configured to mate with second stage 504.

In this example, ends of at least one input optical fiber 120 and at least one output optical fiber 122 are coupled to first stage 506, specifically upper portion 530. As shown, coupling between optical fibers 120, 122 and first stage 506 occurs via one or more position assembly housings 700 such that portions of the housing(s) face one another. This facing relationship allows light signals transmitted via input optical fiber 120 to pass through, or be blocked by, an encoder 126 and the light pattern received by output optical fiber 122. In this example, at least one lens 702 is coupled to one an end of one or both of input optical fiber 120 or output optical fiber 122. The at least one lens 702 is adapted to focus the light to be carried by the respective optical fibers or to focus light onto encoder 126. In one example, the spacing between portions of position assembly housing(s) 700 and encoder 126 is 0.5 mm or less. In another example, portions of the position assembly housing(s) 700 are positioned so as to slight touch encoder 126, which may help reduce the parallax problem often associated with optical systems.

Encoder 126 shown in FIG. 6 is coupled to second stage 504 between optical fibers 120 and 122. As a result of being coupled to second stage 504, encoder 126 is movable relative to position assembly housing(s) 700 and optical fibers 120, 122 and stationary relative to instrument 102 retained by retaining assembly 550A. As discussed above, encoder 126 comprises a translucent substrate and one or more light blocking indicia 406. In one example, such indicia 406 include a linear array of relative position indicia 406B that provide a light pattern pass through indicative of a relative (e.g., to an absolute reference) position of instrument 102. In another example, the one or more light blocking indicia 406 include a linear array of absolute position indicia 406A that provide a light pattern pass through indicative of an absolute position of instrument 102 from, for example, a desired target within brain 118 (FIG. 1).

FIG. 7 is an isometric view illustrating portions of an assembly 100 for remotely detecting a position of one or more surgical instruments 102 (FIG. 1) in the presence of a magnetic field 104 (FIG. 1). Specifically, FIG. 7 illustrates an example of a position assembly housing 700 adapted for use in position detection assembly 100.

As discussed above, an encoder 126 moves with the one or more instruments 102 being introduced into a subject 106 (FIG. 1) by attaching encoder 126 to the instrument 102 itself, or by attaching encoder 126 to an advancing/retracting carriage, such as a second stage 504 (FIG. 6) of a drive and trajectory guide assembly. In varying examples, and as shown, encoder 126 is translucent except for an array of light-blocking indicia 406, such as absolute position indicia 406A or relative position indicia 406B. As also discussed, a light source 128 (FIG. 1) provides light signals (transmitted via at least one input optical fiber 120) that are directed (via one or more lenses 702) to shine through encoder 126 as it is being advanced or retracted in concert with the one or more instruments 102. A light detector array (by way of at least one output optical fiber 122) detects a position of instrument(s) 102 being introduced by reading and decoding the uniquely-identifiable indicia 406 on encoder 126.

One or more position assembly housings 700 may be used to couple optical fibers 120, 122 to an instrument introduction assembly, such as a drive and trajectory guide assembly 124 (FIG. 5), and appropriately direct ends thereof to emit and receive light signals. In the example of FIG. 7, a transmitting/receiving position assembly housing 700 is shown. Housing 700 includes at least one recess in housing portion 700A for holding an end portion of the at least one input optical fiber 120 securable using, for example, an adhesive, and at least one recess 704 (e.g., groove) in housing portion 700B for holding an end portion of the at least one output optical fiber 122. In addition, housing 700 may include one or more (polycarbonate) lenses 702 co-molded within housing 700 to focus light from light source 128 into a beam of such diameter that one of the light blocking indicia 406 (FIG. 4) on encoder 126 obstructs the beam from passing through the translucent scale or to focus received light signals into output optical fiber(s) 122. In one example, housing 700 includes transmitters or receivers such as HFBT-1523 or HFBT-2523 manufactured by Agilent Technologies of Palo Alto, Calif., USA. In another example, housing 700 is composed of a polymer. In this example, housing portion 700B is adapted to connect to housing portion 700A via snap projections 706. Also in the example of FIG. 7, housing 700 includes a step portion 708 into which encoder 126 may move about (e.g., slide).

Figure 8A:
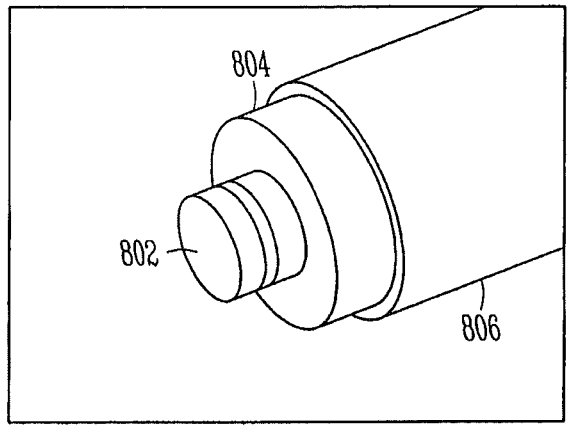
FIG. 8A is an isometric view illustrating components of a single optical fiber, as constructed in accordance with at least one embodiment.
Figure 8B:
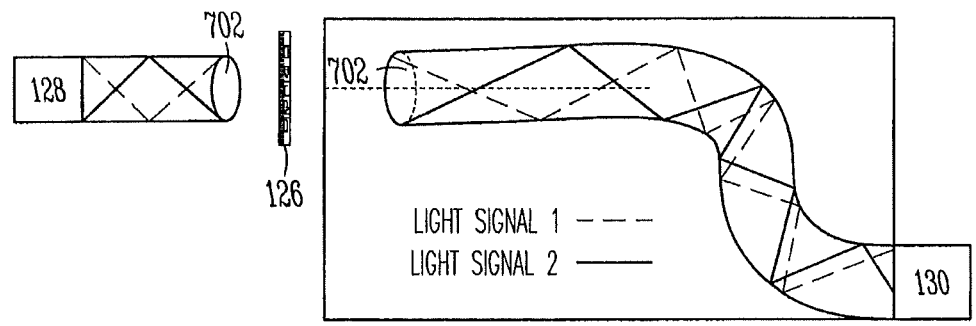
FIG. 8B is a simplified cross-sectional view illustrating total internal reflection in an optical fiber.

FIGS. 8A, 8B are directed toward optical fibers, such as the input optical fiber 120 or the output optical fiber 122 discussed above. Specifically, FIG. 8A illustrates components of a single optical fiber. Each of optical fibers 120, 122, generally speaking, comprises a core 802, a cladding 804, and a buffer coating 806. Core 802 is the thin (glass) center of the fiber where the light signals travel. Cladding 804 is the outer optical material surrounding core 802 that reflects the light back into core 802. Buffer coating 806 is the plastic coating that protects the fiber from damage.

Core 802 and cladding 804 are composed of materials that have different optical transmission properties. An important property of these materials is the index of refraction (typically designed by the letter "n"), a material constant that determines the direction of the light (signals) through the material. The index of refraction of the core 802 must be larger than that of the cladding 804 for the light to travel through the optical fiber. As shown in FIG. 8B, optical fibers 120, 122 allow light signals to be transmitted from light source 128, through one or more lenses 702 and encoder 126, and transmitted to light detector array 130 by constantly bouncing light signals off cladding 804 (FIG. 8A) through core 802 (FIG. 8B) (referred to as "total internal reflection").

Figure 9:
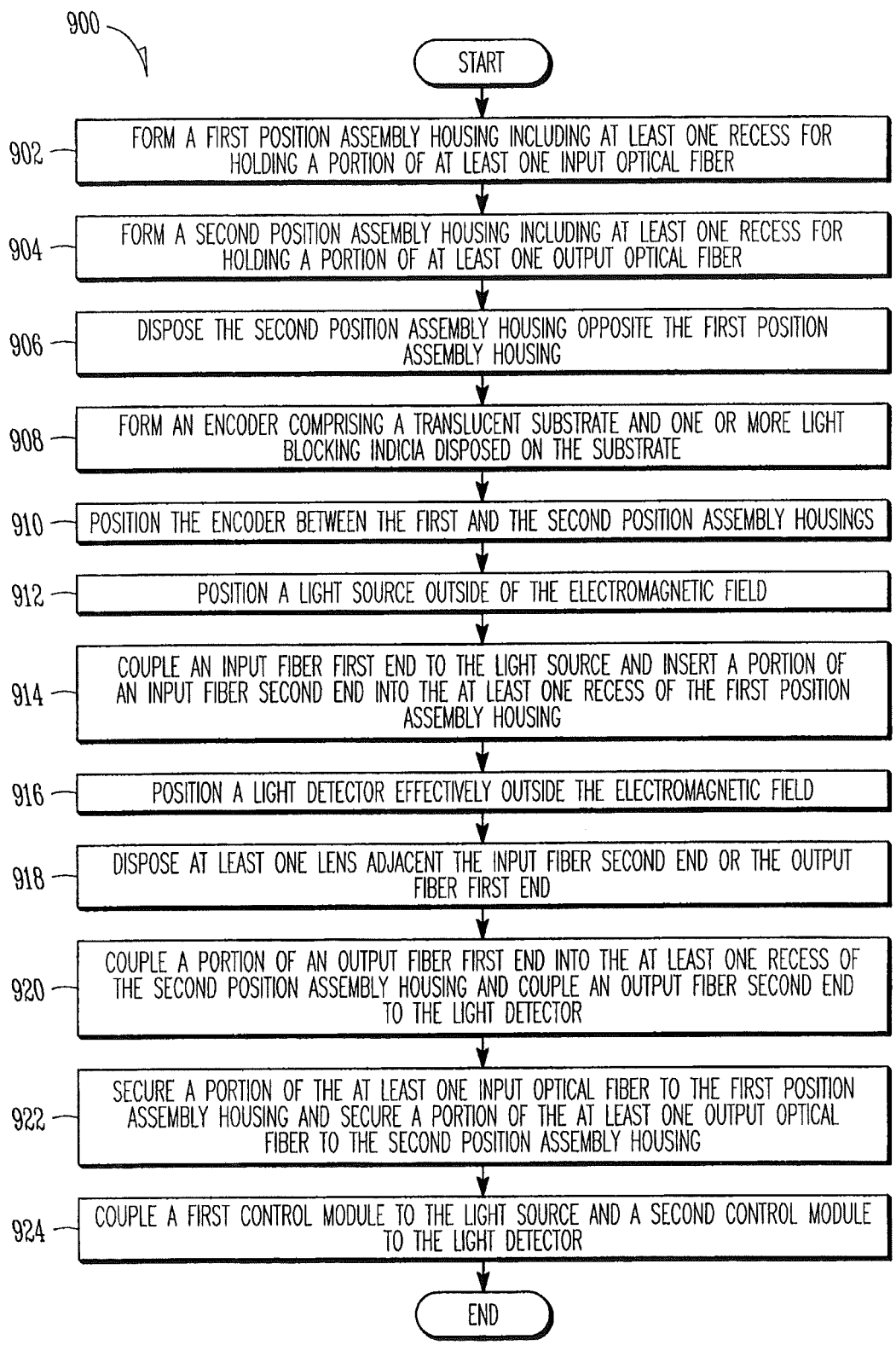
FIG. 9 is a flow diagram illustrating a method of fabricating an assembly for providing remote position detection in a magnetic field, as constructed in accordance with at least one embodiment.

FIG. 9 is a flow diagram illustrating a method 900 of fabricating a position detection assembly operable in a magnetic field. At 902, a first position assembly housing couplable to an instrument introduction assembly (e.g., the drive and trajectory guide assembly discussed above) is formed. Formation of the first position assembly housing includes forming at least one recess for holding an end portion of at least one input optical fiber. At 904, a second position assembly housing couplable to the instrument introduction assembly is formed. Formation of the second position assembly housing includes forming at least one recess for holding an end portion of at least one output optical fiber. In one example, steps 902 and 904 are combined such that the first and second position assembly housings are integrally formed. At 906, the second position assembly housing is disposed (and coupled to the instrument introduction assembly) opposite the first position assembly housing, such that a portion of each assembly housing faces toward one another in an aligned emitting manner.

At 908, an encoder having an encoder first side and an encoder second side is formed. The encoder includes a translucent substrate and one or more light blocking indicia disposed thereon. In varying examples, the first position assembly housing, the second position assembly housing, and the encoder are composed of one or more non-conductive and non-magnetic materials allowing the device to be operable in a magnetic field, such as the field generated by a MRI scanner. At 910, the encoder is positioned between the first and the second position assembly housings. In one such example, the encoder is movably mounted relative to the first or the second position assembly housings. The movable mounting may occur, among other ways, by mounting the encoder to an advancing/retracting carriage of the instrument introduction assembly (e.g., the second stage of the drive and trajectory guide assembly discussed above).

At 912 and 916, a light source and a light detector array, respectively, are positioned effectively outside the magnetic field. At 914, at least one input optical fiber optically couples the light source and a point adjacent the encoder first side. To accomplish this, an input fiber first end is coupled to the light source while an end portion of an input fiber second end is inserted into the at least one recess of the first position assembly housing and secured at 922. In a similar fashion, at 920, at least one output optical fiber optically couples a point adjacent the encoder second side and the light detector array. To accomplish this, an end portion of an output fiber first end is inserted into the at least one recess of the second position assembly housing and secured at 922 and an output fiber second end is coupled to the light detector array. In one example, prior to the output fiber first end being inserted into the at least one recess of the second position assembly housing, at least one lens is disposed adjacent thereto at 918.

Several options for fabricating a position detection assembly housing are possible. In one example, at 924, the method may further comprise coupling a first control module to the light source and a second control module to the light detector array. As another example, the method of fabrication is not limited to the particular order discussed above. As will be appreciated by those skilled in the art, the method of fabricating the position detection assembly may be performed in a variety of ways (e.g., order of steps).

Figure 10:
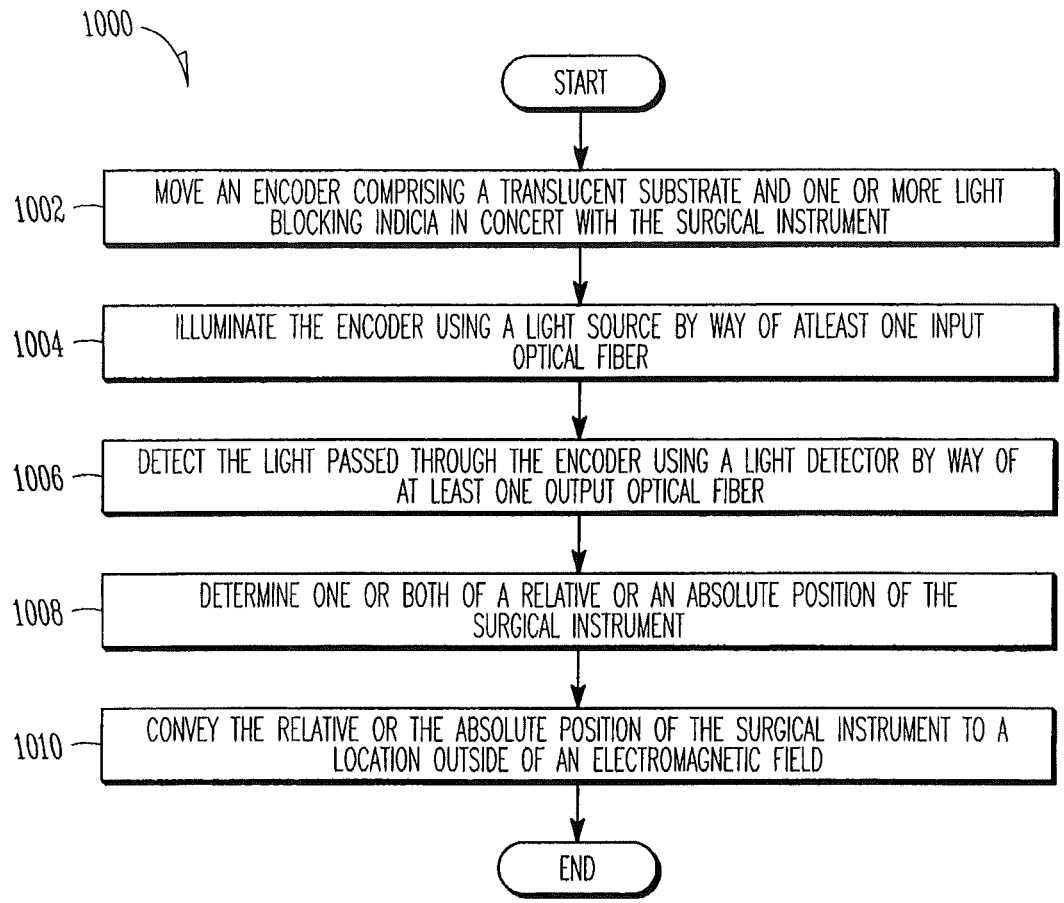
FIG. 10 is a flow diagram illustrating a method of detecting a position of a surgical instrument, as constructed in accordance with at least one embodiment.

FIG. 10 is a flow diagram illustrating a method 1000 of detecting a position of a surgical instrument. At 1002, an encoder comprising a translucent substrate and one or more (unique) light blocking indicia (e.g., relative position indicia or absolute position indicia) is moved in concert with the surgical instrument. At 1004, the encoder is illuminated using a light source and at least one input optical fiber. In one such example, an input fiber first end is coupled to the light source and an input fiber second end is disposed adjacent an encoder first side. As a result, light may be transmitted from the light source and directed through the encoder. Movement of the one or more light blocking indicia disposed on the translucent substrate interrupts such directed light from passing through the encoder.

At 1006, the light passing through the encoder is detected using a light detector array and at least one output optical fiber. Detection of the light passing through may include, among other things, detecting the number of times that the light source is interrupted by the one or more light blocking indicia. At 1008, one or both of the relative or the absolute position of the surgical instrument is determined. Such determination includes the decoding of the detected light passing through a different part of the encoder. At 1010, the relative or absolute position of the surgical instrument is conveyed to a location outside of a magnetic field, such as a RF-field associated with a MRI scanner. In one example, the determination and conveyance of the position of the surgical instrument is performed using a control module coupled with the light detector array.

To recap, the present assemblies and methods provide real time remote position (e.g., depth) information of one or more surgical instruments (located within the typically strong magnetic field associated with MR imaging) to a surgeon (effectively) located outside of the magnetic field. Although the present assemblies and methods have been discussed for utilization with neurosurgical apparatus, such assemblies and methods are not so limited. It will be appreciated by those skilled in the art that the present assemblies and methods may be utilized with other diagnostic or treatment apparatus, and that the magnetic environment about the subject may be an electrical/magnetic field other than an RF-field or similar created by a MRI scanner.

Advantageously, the present assemblies and methods include many other desirable characteristics including adequate patient isolation (e.g., from eddy currents) with good instrument performance. In addition, the present assemblies and methods are easy and economical to manufacture, maintain, and use.

It is to be understood that the above description is intended to be illustrative, and not restrictive. For example, the above detailed description may be used in combination with each other. Many other embodiments will be apparent to those of skill in the art upon reading and understanding the above description. The scope of the invention should, therefore, be determined with reference to the appended claims, along with the full scope of legal equivalents to which such claims are entitled. In the appended claims, the term "including" is used as the plain-English equivalent of the term "comprising." Also, in the following claims, the terms "including" and "comprising" are open-ended, that is, a system, assembly, device, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing detailed description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate embodiment.

The invention claimed is:

1. A neurosurgical system providing position detection in a MRI environment, the system comprising:
   a drive and trajectory guide assembly including:
      a base defining an instrument trajectory;
      a first stage coupled to the base along the trajectory; and
      a second stage movably coupled to the first stage and operable to move one or more surgical instruments coupled thereto with respect to the base and the first stage; and
   a position detection assembly including:
      an encoder coupled to the second stage, the encoder comprising a translucent substrate and one or more light blocking indicia disposed thereon;
      a light source coupled to a first control module adapted to provide one or more electrical signals to the light source;
      at least one input optical fiber coupled to the light source on an input fiber first end and disposed at a point adjacent an encoder first side on an input fiber second end;
      a light detector array coupled to a second control module adapted to receive one or more electrical signals produced by the light detector array;

at least one output optical fiber disposed at a point adjacent an encoder second side on an output fiber first side and coupled to the light detector on an output fiber second side; and wherein the input fiber second end and the output fiber first end are stationarily mounted relative to the base and the first stage.

2. The neurological system as recited in claim 1, wherein the first and the second control modules are integral with one another.

3. The neurological system as recited in claim 1, wherein one or both the first or the second control modules include a display.

4. The neurological system as recited in claim 1, further comprising a position assembly housing including at least one recess adapted to hold a portion of one or both of the at least one input optical fiber or the at least one output optical fiber;

wherein more or more lenses are disposed in the housing near an end of the at least one input or output optical fiber; and wherein the housing is coupled to the drive and trajectory guide assembly.

5. The neurological system as recited in claim 4, wherein the encoder is stationarily coupled to the second stage.

6. The neurological system as recited in claim 1, wherein the encoder first side is opposite the encoder second side.

7. A method of detecting a position of a surgical instrument, the method comprising:

moving an encoder including a translucent substrate and one or more light blocking indicia in concert with the surgical instrument;

illuminating the encoder using a light source by way of at least one input optical fiber, wherein movement of the one or more light blocking indicia disposed on the translucent substrate interrupts light from passing through the encoder;

detecting the light passed through the encoder using a light detector array by way of at least one output optical fiber;

determining one or both of a relative or an absolute position of the surgical instrument based on the detecting light passed through the encoder, wherein determining the position of the surgical instrument includes decoding the light detected through the encoder;

wherein detecting the light passed through the encoder includes detecting a unique pattern of light passed through the encoder; and wherein determining one or both of a relative or an absolute position of the surgical instrument based on the detecting light passed through the encoder includes determining an absolute position of the surgical instrument based on an absolute position indicia that creates the detected unique pattern of light.

8. The method as recited in claim 7, wherein detecting the light passed through the encoder includes detecting the number of times that the light source is interrupted by the one or more light blocking indicia.

9. The method as recited in claim 7, further comprising conveying the relative or the absolute position of the surgical instrument to a location outside of a magnetic field when the surgical instrument is within the magnetic field.

10. The method as recited in claim 9, wherein conveying the position of the surgical instrument includes indicating the position on a display.

11. The method as recited in claim 7, further comprising stationarily mounting the encoder relative to the surgical instrument within the magnetic field.

12. A method of detecting a position of a surgical instrument, the method comprising:

moving an encoder including a translucent substrate and one or more light blocking indicia in concert with the surgical instrument;

illuminating the encoder using a light source by way of at least one input optical fiber, wherein movement of the one or more light blocking indicia disposed on the translucent substrate interrupts light from passing through the encoder;

detecting the light passed through the encoder using a light detector array by way of at least one output optical fiber;

determining one or both of a relative or an absolute position of the surgical instrument based on the detecting light passed through the encoder, wherein determining the position of the surgical instrument includes decoding the light detected through the encoder; and positioning the encoder between a first position assembly housing and a second position assembly housing, wherein the at least one input optical fiber is held by the first position assembly housing and the at least one output optical fiber is held by the second position assembly housing.

13. The method as recited in claim 12, further comprising:

movably mounting the encoder relative to at least one of the first position assembly housing or the second position assembly housing.

* * * * *